US012246071B2

(12) United States Patent
Arima et al.

(10) Patent No.: US 12,246,071 B2
(45) Date of Patent: Mar. 11, 2025

(54) BRAIN-PENETRATING LIGAND AND DRUG CARRIER

(71) Applicants: NATIONAL UNIVERSITY CORPORATION KUMAMOTO UNIVERSITY, Kumamoto (JP); NIHON SHOKUHIN KAKO CO., LTD., Tokyo (JP)

(72) Inventors: Hidetoshi Arima, Kumamoto (JP); Keiichi Motoyama, Kumamoto (JP); Taishi Higashi, Kumamoto (JP); Risako Onodera, Kumamoto (JP); Ryoma Yokoyama, Kumamoto (JP)

(73) Assignees: NATIONAL UNIVERSITY CORPORATION KUMAMOTO UNIVERSITY, Kumamoto (JP); NIHON SHOKUHIN KAKO CO., LTD., Tokyo (JP)

( * ) Notice: Subject to any disclaimer, the term of this patent is extended or adjusted under 35 U.S.C. 154(b) by 758 days.

(21) Appl. No.: 17/419,068

(22) PCT Filed: Dec. 27, 2019

(86) PCT No.: PCT/JP2019/051421
§ 371 (c)(1),
(2) Date: Jun. 28, 2021

(87) PCT Pub. No.: WO2020/138421
PCT Pub. Date: Jul. 2, 2020

(65) Prior Publication Data
US 2022/0072150 A1 Mar. 10, 2022

(30) Foreign Application Priority Data

Dec. 27, 2018 (JP) ................................ 2018-245538
Apr. 25, 2019 (JP) ................................ 2019-084043

(51) Int. Cl.
*A61K 47/69* (2017.01)
(52) U.S. Cl.
CPC ................................ *A61K 47/6951* (2017.08)
(58) Field of Classification Search
None
See application file for complete search history.

(56) References Cited

U.S. PATENT DOCUMENTS

| | | |
|---|---|---|
| 5,002,935 A | 3/1991 | Bodor |
| 2003/0119761 A1* | 6/2003 | Christian ............ A61K 9/2018 424/449 |
| 2018/0264025 A1 | 9/2018 | Jono et al. |

FOREIGN PATENT DOCUMENTS

| | | |
|---|---|---|
| JP | 1-294663 A | 11/1989 |
| JP | 7-126162 A | 5/1995 |
| JP | 2011-103811 A | 6/2011 |
| WO | 2016/199892 A1 | 12/2016 |

OTHER PUBLICATIONS

Murthy, R. V., Bavireddi, H., Gade, M., & Kikkeri, R. (2015). Exploiting the Lactose—GM3 Interaction for Drug Delivery. ChemMedChem, 10(5), 792-796. (Year: 2015).*
"Prevention" in Glossary of medical education terms: Parts 1-7. Wojtczak, A., Ed. Medical Teacher. vol. 24, Nos. 2-6 and vol. 25, No. 1&2. 2002. (Year: 2002).*
Anraku et al., "Glycaemic control boosts glucosylated crossing the BBB into the brain nanocamer" Nat. Commun. Oct. 17, 2017, 8(1):1001.
He et al., "PEGylated Poly(amidoamine) dendrimer-based dual-targeting carrier for treating brain tumors" Biomaterials, Jan. 2011;32(2):478-87.
Hayasi et al., "Potential Use of Lactosylated Dendrimer (G3)/α-Cyclodextrin Conjugates as Hepatocyte-Specific siRNA Carriers for the Treatment of Familial Amyloidotic Polyneuropathy" Mol Pharma. 9, 1645-1653, 2012.
Motoyama et al., "Synthesis of multi-lactose-appended β-cyclodextrin and its cholesterol-lowering effects in Niemann—Pick type C disease-like HepG2 cells" Beilstein J Org. Chem. 13, 10-18, 2017.
Yuki Maeda et al., "In Vivo Evaluation of Lactosyl-β-cyclodextrin as a Therapeutic Agent for Niemann-Pick Type C Disease," vol. 138, Item of 27W-am12, Abstracts of the 138th Annual Meeting of the Pharmaceutical Society of Japan, Mar. 25, 2018, and English translation thereof.
Madoka Fukaura et al., "Optimization of Intracerebroventricular 2-Hydroxypropyl-β-cyclodextrin Therapy against Niemann-Pick Disease Type C," vol. 26, p. 196, Item S17-3, Proceedings of the 26th Clinical Pharmacy Symposium, Medical Pharmacy Forum 2018, Jul. 24, 2018 and English translation thereof.
Ryoma Yokoyama, "Possibility evaluation of lactose-modified cyclodextrin for construction of brain-localized drug carrier," Proceedings of the 35th Annual Meeting of the Japan Society of Drug Delivery System, Item of 2-3-11, Jun. 15, 2019 and English translation thereof.
English translation of ISR for International Patent Application No. PCT/JP2019/051421 mailed on Feb. 10, 2020.

(Continued)

*Primary Examiner* — Dale R Miller
(74) *Attorney, Agent, or Firm* — Hunton Andrews Kurth LLP

(57) ABSTRACT

An exemplary substance is provided that permeates the blood-brain barrier and shows a property of penetrating into the brain. Further, exemplary use of the substance as a drug carrier is provided for delivering into the brain, and a pharmaceutical composition containing the substance. Additionally, exemplary lactose-modified cyclodextrin or dendrimer/glucuronyl glucosyl-cyclodextrin is provided that permeates the blood-brain barrier and shows a property of penetrating into the brain. Exemplary blood-brain barrier permeable pharmaceutical composition is also provided which comprises a lactose-modified cyclodextrin or dendrimer/glucuronyl glucosyl-cyclodextrin, and a drug.

21 Claims, 11 Drawing Sheets

(56) References Cited

OTHER PUBLICATIONS

English translation of Written Opinion of ISA for International Patent Application No. PCT/JP2019/051421 mailed on Feb. 10, 2020.
English Translation of International Search Report for International Patent Application No. PCT/JP2019/051421 mailed on Feb. 10, 2020.

* cited by examiner a : Lac-GUG-β-CDE (G3, DS3, DSL7)
b : Lactose

① Saline
② 5 min
③ 10 min
④ 30 min
⑤ 60 min
⑥ 180 min a : Lactose
b : NH$_2$-HP-β-CyD
c : Sample

BRAIN-PENETRATING LIGAND AND DRUG CARRIER

This application relates to, and claims the benefit and priority from International Patent Application No. PCT/JP2019/051421 filed on Dec. 27, 2019, and published as International Publication WO 2020/138421 on Jul. 2, 2020, which claims the benefit and priority from Japanese Patent Application No. 2018-245538 filed on Dec. 27, 2018 and Japanese Patent Application No. 2019-084043 filed on Apr. 25, 2019, the entire disclosures of all of which are incorporated herein by reference in their entireties.

TECHNICAL FIELD

The present invention relates to a novel substance that permeates the blood-brain barrier and exhibits a property of penetrating into the brain. The present invention also relates to the use of the substance as a drug carrier for intracerebral delivery, and a pharmaceutical composition comprising the substance.

BACKGROUND ART

Intractable brain diseases such as Alzheimer's disease and malignant brain tumors are diseases in which there are few effective treatment methods and the contribution of drugs to the treatment is low. For the treatment of these brain diseases, it is necessary to effectively deliver drugs into the brain. However, since the brain has the blood-brain barrier (BBB), if a drug is administered orally or by injection, it is more difficult to obtain effective drug concentrations than in other organs. On the other hand, when trying to achieve an effective concentration in the brain by high-dose administration, a large excess of the drug is present in the peripheral blood, which causes side effects such as renal and liver disorders. In this way, the obstacle to developments of therapeutic agents for brain diseases including intractable brain diseases is a strong biological barrier called the blood-brain barrier, which acts as a physical and dynamic barrier that separates blood from brain tissue fluid, strictly limiting passive diffusion of substances into the brain. Therefore, in order to deliver a target substance administered in the blood into the brain, it is necessary to develop an intracerebral penetrating ligand or a drug carrier for intracerebral delivery for efficiently permeating the blood-brain barrier.

The vascular endothelial cells of the brain form a special structure in which the intercellular spaces provide tight junctions, and blood components hardly permeate through the intercellular spaces. As one methodology for achieving delivery into the brain, targeting membrane surface proteins expressed on cerebrovascular endothelial cells has been proposed and developed. That is, it is a method of utilizing the function of a protein called a transporter that exists on the membrane surface for the uptake of a drug into the brain. So far, drug carriers have been developed using brain-penetrating ligands such as glucose, insulin, transferrin and the like, targeting the glucose receptors, the insulin receptor, the transferrin receptor and the like expressed on cerebrovascular endothelial cells.

Examples of the above materials include, for example, a monoclonal antibody against the transferrin receptor (J-Brain Cargo (registered trademark) available from JCR Pharmaceuticals Co., Ltd.), a monoclonal antibody against the insulin receptor, and the like. Further, a high molecular weight micelle having a diameter of about 30 nm obtained by modifying glucose, which is a kind of intracerebral penetrating ligand, has been proposed (Non-Patent Document 1: Anraku et al., Nat. Commun. 2017 Oct. 17, 8 (1): 1001). It is suggested that when this micelle is intravenously administered to fasting mice and a glucose solution is administered 30 minutes later, the micelle is transcytosed at the blood-brain barrier and up to about 6% of the dose accumulates in the brain. Furthermore, it is shown that the micelle is significantly taken up by nerve cells in the brain after permeation through the blood-brain barrier. However, since it is needed to administer the micelle in the fasted state and further to administer also a glucose solution, this technology has many restrictions when considering actual clinical use.

Furthermore, it has been reported that a blood-brain barrier permeable nanocarrier (Tf-WGA-PAMAM-PEG) was constructed by modifying doxorubicin-enclosing dendrimer (G4) with PEG (PAMAM-PEG) and further imparting a brain-penetrating ligand transferrin (Tf) and wheat germ agglutinin (WGA) (Non-Patent Document 2: He et al., Biomaterials, 2011 January; 32 (2): 478-87). The blood-brain barrier permeability of Tf-WGA-PAMAM-PEG in the in vitro BBB model was increased approximately 2-fold compared to PAMAM-PEG. However, no studies have been conducted in vivo, and further, Tf and WGA are very expensive. Moreover, since these ligands have a high molecular weight, modification of the carriers significantly changes the properties of the carriers themselves. In addition, the proteinaceous ligand has a problem in terms of safety and quality since it may aggregate by physicochemical stimuli.

As a different approach from the above, a Drug Delivery System (DDS) using a blood-brain barrier permeation carrier such as Tat, RVG-9R peptide, RDP peptide, Angiopep and the like, which DDSs use a cellular membrane permeating peptide has also been proposed.

Although various drug carriers have been developed as described above, the delivery efficiency into the brain is still insufficient, and the search for a new brain-penetrating ligand or a drug carrier for intracerebral delivery is an issue.

The present inventors have planned to construct a carrier targeting the liver and constructed and reported a lactose-modified dendrimer/α-cyclodextrin conjugate (Non-Patent Document 3: Hayasi et al., Mol Pharma. 9, 1645-1653, 2012). Furthermore, the present inventors have reported lactose-modified β-cyclodextrin for the purpose of constructing a liver-penetrating cyclodextrin designed for the treatment of hepatosplenomegaly in Niemann-Pick disease type C (Non-Patent Document 4: Motoyama et al., Beilstein J Org. Chem. 13, 10-18, 2017).

CITATION LIST

Non-Patent Documents

Non-Patent Document 1: Anraku et al., Nat. Commun. 2017 Oct. 17, 8(1):1001

Non-Patent Document 2: He et al., Biomaterials, 2011 January; 32(2):478-87

Non-Patent Document 3: Hayasi et al., Mol Pharma. 9, 1645-1653, 2012

Non-Patent Document 4: Motoyama et al., Beilstein J Org. Chem. 13, 10-18, 2017

SUMMARY OF THE INVENTION

Technical Problem

The present invention is to provide a novel substance having blood-brain barrier permeability.

Solution to Problem

The present inventors have made intensive studies in order to solve the problem, and resultantly found that by modifying cyclodextrin or dendrimer/glucuronyl glucosyl-cyclodextrin with lactose, it becomes possible to permeate the blood-brain barrier, completing the present invention.

The present invention includes the followings.

[1] A pharmaceutical composition comprising a lactose-modified cyclodextrin or a derivative thereof, and a drug, wherein the lactose-modified cyclodextrin or a derivative thereof is contained to increase the blood-brain barrier permeability of the drug.

[2] The pharmaceutical composition according to [1], wherein the lactose-modified cyclodextrin or a derivative thereof is a lactose-modified β-cyclodextrin or a lactose-modified dendrimer/glucuronyl glucosyl-β-cyclodextrin.

[3] A pharmaceutical composition comprising a lactose-modified cyclodextrin or a derivative thereof, and a drug, wherein the drug is delivered into the brain by the lactose-modified cyclodextrin or a derivative thereof.

[4] The pharmaceutical composition according to [3], wherein the lactose-modified cyclodextrin or a derivative thereof is a lactose-modified p-cyclodextrin or a lactose-modified dendrimer/glucuronyl glucosyl-β-cyclodextrin.

[5] The pharmaceutical composition according to [1] or [3], wherein the lactose-modified cyclodextrin or a derivative thereof is a lactose-modified dendrimer/glucuronyl glucosyl-β-cyclodextrin.

[6] The pharmaceutical composition according to [5], wherein the lactose-modified dendrimer/glucuronyl glucosyl-β-cyclodextrin is one in which at least the dendrimer molecule is modified with lactose.

[7] The pharmaceutical composition according to [5] or [6], wherein the degree of substitution of cyclodextrin against dendrimer in the lactose-modified dendrimer/glucuronyl glucosyl-β-cyclodextrin is 1 to 10, preferably 2 to 8, more preferably 2 to 6.

[8] The pharmaceutical composition according to any one of [1] to [7], wherein the degree of substitution of lactose against cyclodextrin or dendrimer in the lactose-modified cyclodextrin or a derivative thereof is 1 or more, preferably 2 to 8, more preferably 3 to 7.

[9] A carrier for drug delivery into the brain comprising a lactose-modified cyclodextrin or a derivative thereof.

[10] The carrier for drug delivery according to [9], wherein the lactose-modified cyclodextrin or a derivative thereof is a lactose-modified β-cyclodextrin or a lactose-modified dendrimer/glucuronyl glucosyl-β-cyclodextrin.

[11] The carrier for drug delivery according to [9], wherein the lactose-modified cyclodextrin or a derivative thereof is a lactose-modified dendrimer/glucuronyl glucosyl-β-cyclodextrin.

[12] The carrier for drug delivery according to [11], wherein the lactose-modified dendrimer/glucuronyl glucosyl-β-cyclodextrin is one in which at least the dendrimer molecule is modified with lactose.

[13] The carrier for drug delivery according to [11] or [12], wherein the degree of substitution of cyclodextrin against dendrimer in the lactose-modified dendrimer/glucuronyl glucosyl-β-cyclodextrin is 1 to 10, preferably 2 to 8, more preferably 2 to 6.

[14] The carrier for drug delivery according to any one of [9] to [13], wherein the degree of substitution of lactose against cyclodextrin or dendrimer in the lactose-modified cyclodextrin or a derivative thereof is 1 or more, preferably 2 to 8, more preferably 3 to 7.

[15] The carrier for drug delivery according to any one of [9] to [14], wherein the carrier is used for delivering a drug into the brain through the blood-brain barrier.

[16] A complex consisting of a drug to be delivered into the brain and a lactose-modified cyclodextrin or a derivative thereof.

[17] The complex according to [16], wherein the lactose-modified cyclodextrin or a derivative thereof is a lactose-modified β-cyclodextrin or a lactose-modified dendrimer/glucuronyl glucosyl-β-cyclodextrin.

[18] The complex according to [16], wherein the lactose-modified cyclodextrin or a derivative thereof is a lactose-modified dendrimer/glucuronyl glucosyl-β-cyclodextrin.

[19] The complex according to [18], wherein the lactose-modified dendrimer/glucuronyl glucosyl-3-cyclodextrin is one in which at least the dendrimer molecule is modified with lactose.

[20] The complex according to [18] or [19], wherein the degree of substitution of cyclodextrin against dendrimer in the lactose-modified dendrimer/glucuronyl glucosyl-β-cyclodextrin is 1 to 10, preferably 2 to 8, more preferably 2 to 6.

[21] The complex according to any one of [16] to [20], wherein the degree of substitution of lactose against cyclodextrin or dendrimer in the lactose-modified cyclodextrin or a derivative thereof is 1 or more, preferably 2 to 8, more preferably 3 to 7.

[22] The complex according to any one of [16] to [21], wherein the drug is delivered into the brain through the blood-brain barrier.

[23] A brain-penetrating ligand for delivering a drug into the brain of subject, wherein the brain-penetrating ligand has a binding affinity to a transporter or a receptor that recognizes a lactose expressed in brain endothelial cells and contains lactose as a part of its molecule.

[24] The brain-penetrating ligand according to [23], wherein the brain-penetrating ligand is a lactose-modified cyclodextrin or a derivative thereof.

[25] The brain-penetrating ligand according to [24], wherein the lactose-modified cyclodextrin or a derivative thereof is a lactose-modified β-cyclodextrin or a lactose-modified dendrimer/glucuronyl glucosyl-β-cyclodextrin.

[26] The brain-penetrating ligand according to [24], wherein the lactose-modified cyclodextrin or a derivative thereof is a lactose-modified dendrimer/glucuronyl glucosyl-β-cyclodextrin.

[27] The brain-penetrating ligand according to [26], wherein the lactose-modified dendrimer/glucuronyl glucosyl-β-cyclodextrin is one in which at least the dendrimer molecule is modified with lactose.

[28] The brain-penetrating ligand according to [26] or [27], wherein the degree of substitution of cyclodextrin against dendrimer in the lactose-modified dendrimer/glucuronyl glucosyl-β-cyclodextrin is 1 to 10, preferably 2 to 8, more preferably 2 to 6.

[29] The brain-penetrating ligand according to any one of [23] to [28], wherein the degree of substitution of lactose against cyclodextrin or dendrimer in the lactose-modified cyclodextrin or a derivative thereof is 1 or more, preferably 2 to 8, more preferably 3 to 7.

[30] Use of the brain-penetrating ligand according to any one of [23] to [29].

[31] A lactose-modified dendrimer/glucuronyl glucosyl-β-cyclodextrin.

[32] The lactose-modified dendrimer/glucuronyl glucosyl-β-cyclodextrin according to [31], wherein at least the dendrimer molecule is modified with lactose.

[33] The lactose-modified dendrimer/glucuronyl glucosyl-β-cyclodextrin according to [31] or [32], wherein the degree of substitution of cyclodextrin against dendrimer is 1 to 10, preferably 2 to 8, more preferably 2 to 6 and the degree of substitution of lactose against cyclodextrin or dendrimer is 1 or more, preferably 2 to 8, more preferably 3 to 7.

[34] The pharmaceutical composition according to any one of [1] to [8] for preventing or treating a cranial nerve system disease or disorder.

[35] The pharmaceutical composition according to [34], wherein the cranial nerve system disease or disorder is selected from the group consisting of Alzheimer's disease, malignant brain tumor, Parkinson's disease, Niemann-Pick disease type C, cerebral stroke, cerebral ischemia, dementia, muscular dystrophy, multiple sclerosis, amyotrophic lateral sclerosis, cystic fibrosis, Angelman's syndrome, Riddle Syndrome, myasthenia gravis, spinal muscle atrophy, Down's syndrome, Huntington's disease, schizophrenia, depression, Tauopathy disease, Pick's disease, Paget's disease, lysosome disease accompanied by brain damage, cancer, prion's disease, traumatic brain injury, and viral or bacterial central nervous system disorders.

[36] A method of administering a drug to a patient in need of administration of the drug into the brain, comprising administering to the patient a composition comprising a lactose-modified cyclodextrin or a derivative thereof and a drug encapsulated in the cyclodextrin or a derivative thereof.

[37] The method according to [36], wherein the lactose-modified cyclodextrin or a derivative thereof is a lactose-modified β-cyclodextrin or a lactose-modified dendrimer/glucuronyl glucosyl-β-cyclodextrin.

[38] The method according to [36], wherein the lactose-modified cyclodextrin or a derivative thereof is a lactose-modified dendrimer/glucuronyl glucosyl-3-cyclodextrin.

[39] The method according to [38], wherein the lactose-modified dendrimer/glucuronyl glucosyl-3-cyclodextrin is one in which at least the dendrimer molecule is modified with lactose.

[40] The method according to [38] or [39], wherein the degree of substitution of cyclodextrin against dendrimer in the lactose-modified dendrimer/glucuronyl glucosyl-β-cyclodextrin is 1 to 10, preferably 2 to 8, more preferably 2 to 6.

[41] The method according to any one of [36] to [40], wherein the degree of substitution of lactose against cyclodextrin or dendrimer in the lactose-modified cyclodextrin or a derivative thereof is 1 or more, preferably 2 to 8, more preferably 3 to 7.

[42] The method according to any one of [36] to [41], wherein the drug is delivered into the brain through the blood-brain barrier.

[43] The method according to any one of [36] to [42], wherein the patient is a patient suffering from a neurological disease or disorder.

[44] The method according to [43], wherein the neurological disease or disorder is selected from the group consisting of Alzheimer's disease, cerebral stroke, cerebral ischemia, dementia, muscular dystrophy, multiple sclerosis, amyotrophic lateral sclerosis, cystic fibrosis, Angelman's syndrome, Riddle Syndrome, myasthenia gravis, spinal muscle atrophy, Down's syndrome, Parkinson's disease, Huntington's disease, schizophrenia, depression, Tauopathy disease, Pick's disease, Paget's disease, lysosome disease accompanied by brain damage, cancer, prion's disease, traumatic brain injury, and viral or bacterial central nervous system disorders.

Advantageous Effect of the Invention

The present invention provides a substance that permeates the blood-brain barrier and exhibits a property of penetrating into the brain, and its use.

DESCRIPTION OF EMBODIMENTS

Figure 1:
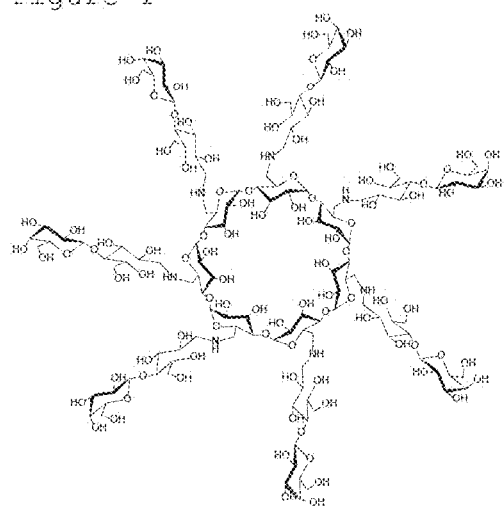
FIG. 1 shows an example of the structure of β-cyclodextrin modified with lactose.

Hereinafter, the present invention will be illustrated and described in detail with reference to the exemplary embodiments, along with the preferred methods and materials which can be used in practice of the present invention. Unless otherwise specified in the sentences, any technical terms and scientific terms used in the present specification, have the same meaning as those generally understood by those of ordinary skill in the art to which the present invention belongs. Any materials and methods equivalent or similar to those described in the present specification can be used for practicing the present invention. All publications and patents cited herein in connection with the present invention described herein are incorporated herein by reference, for example, as indicating methodology, materials, etc. that can be used in the present invention.

In the present specification, when the expression "X to Y" is used, it is used to mean that X is included as the upper limit and Y is included as the upper limit, or that X is included as the lower limit and Y is included as the upper limit. As used herein, the term "about" is used to mean that ±10% is allowed.

(1) Lactose-Modified Cyclodextrin

Cyclodextrin is an oligosaccharide in which 6, 7 or 8 glucoses are linked in a ring shape, and is called α-cyclodextrin, β-cyclodextrin, and γ-cyclodextrin, respectively.

The lactose-modified cyclodextrin that can be used in the present invention is a compound in which hydroxyl groups of cyclodextrin (α-cyclodextrin, β-cyclodextrin, or γ-cyclodextrin) are randomly replaced with lactose, and for example, lactose-modified β-cyclodextrin is a compound in which 6-position hydroxyl groups of the seven glucoses of β-cyclodextrin are randomly replaced with lactose. The lactose-modified cyclodextrin is preferably a lactose-modified β-cyclodextrin. Cyclodextrins modified with lactose include any of either chemically modified or unmodified α, β, or γcyclodextrins. Common methods for chemically modifying cyclodextrin include, for example, methylation, hydroxyalkylation with such as hydroxyethyl or hydroxypropyl, glucosylation, maltosylation, alkylation, acylation, acetylation, sulfation, sulfobutylation, carboxymethylation, carboxyethylation, amination, carboxylation, tosylation, dimethylacetylation and the like. Thus, as used in the present specification, the term lactose-modified cyclodextrin is used to include lactose-modified chemically modified or unmodified α, β, or γcyclodextrins.

The chemically modified cyclodextrin that constitutes a part of the lactose-modified cyclodextrin that can be used in the present invention can be an arbitrary chemically modified cyclodextrin as long as there is no problem of toxicity or the like when administered to a living body. For example, the following chemically modified cyclodextrins can be used. Examples thereof include methyl-α-cyclodextrin; ethyl-α-cyclodextrin; amino-α-cyclodextrin; p-toluenesulfonyl-α-cyclodextrin; hydroxyalkyl-α-cyclodextrin; sulfoalkyl ether-α-cyclodextrin; carboxyalkyl-α-cyclodextrin; azido-α-cyclodextrin; maltosyl-α-cyclodextrin; glucosyl-α-cyclodextrin; glucuronyl glucosyl-α-cyclodextrin; methyl-β-cyclodextrin; ethyl-β-cyclodextrin; amino-β-cyclodextrin; p-toluenesulfonyl-β-cyclodextrin; hydroxyalkyl-β-cyclodextrin; sulfoalkyl ether-β-cyclodextrin; carboxyalkyl-β-cyclodextrin; azido-β-cyclodextrin; maltosyl-β-cyclodextrin; glucosyl-β-cyclodextrin; glucuronyl glucosyl-β-cyclodextrin; methyl-γ-cyclodextrin; ethyl-γ-cyclodextrin; amino-γ-cyclodextrin; p-toluenesulfonyl-γ-cyclodextrin; hydroxyalkyl-γ-cyclodextrin; sulfoalkyl ether-γ-cyclodextrin; carboxyalkyl-γ-cyclodextrin; azido-γ-cyclodextrin; maltosyl-γ-cyclodextrin; glucosyl-γ-cyclodextrin; glucuronyl glucosyl-γ-cyclodextrin and the like. It is preferably β-cyclodextrin, hydroxyalkyl-β-cyclodextrin or glucuronyl glucosyl-β-cyclodextrin (GUG-β-CyD), and further preferably hydroxypropyl-β-cyclodextrin or GUG-β-CyD.

The degree of substitution of lactose against cyclodextrin in a lactose-modified cyclodextrin is not particularly limited, but is at least 1 or more, preferably 2 to 8, and further preferably 3 to 7. FIG. 1 shows the structure of one example of the lactose-modified β-cyclodextrin, where hydroxyl groups are replaced with lactose in all, that is 7 glucoses, and the degree of substitution of lactose (DSL) is 7.0.

Substitution of lactose can be performed with reference to known reports, and examples thereof include, but not limited to, the report by the present inventors (Non-Patent Document 4). This document is incorporated herein by reference.

Figure 2:
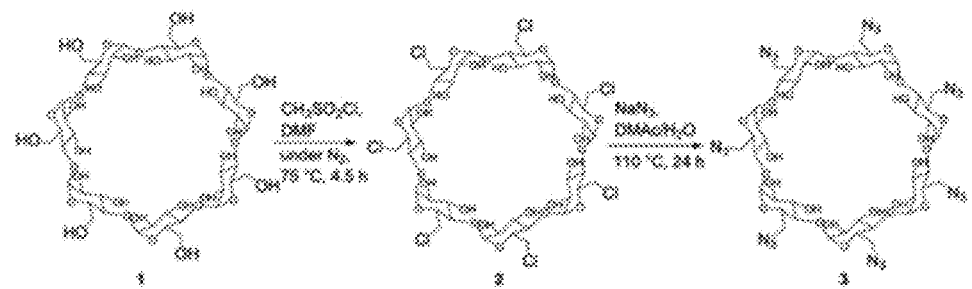
FIG. 2 shows an example of the synthetic pathway that modifies β-cyclodextrin with lactose. 1: β-cyclodextrin (β-CyD), 2: chloro-β-CyD, 3: azide-β-CyD, 4: amino-β-CyD, and 5: lactose-modified β-CyD.
Figure 2:
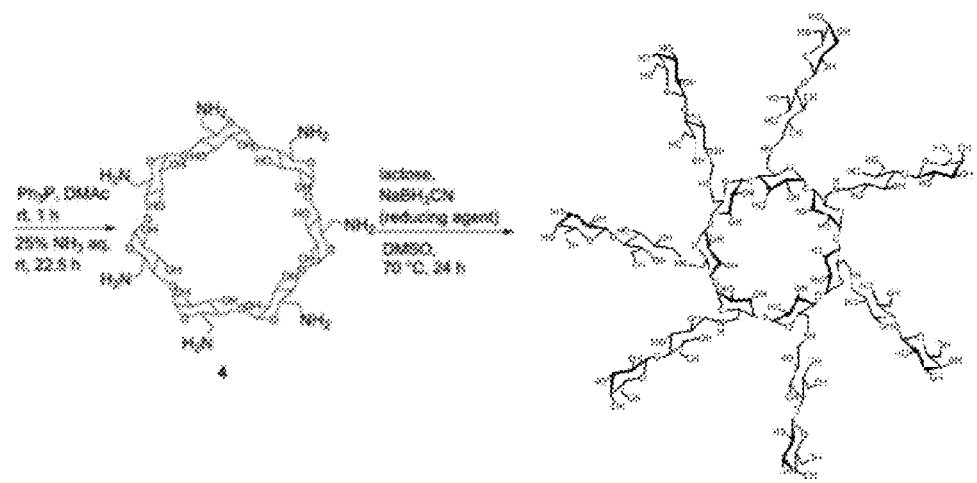

Although not limited to this, for example, when lactose-modification is performed using β-cyclodextrin as an example, as shown in FIG. 2, the hydroxyl group at the 6-position of glucose of cyclodextrin is replaced with an amino group, and then, sodium cyanoborohydride (NaBH$_3$CN) is used and a reductive amination reaction is performed with the hydroxyl group at the 1-position of lactose, thus, cyclodextrin can be modified with lactose.

Cyclodextrin can also be lactose-modified using other synthetic methods, for example, using N-Propargyl-β-lactosylamide, where cyclodextrin and lactose are bound with triazolyl as a binder (Chwalek et al., Org. Biomol. Chem., 2009, 7, 1680-1688). Furthermore, lactose can also be attached to cyclodextrin using any linker.

(2) Lactose-Modified Dendrimer/Cyclodextrin Conjugate

The lactose-modified dendrimer/cyclodextrin conjugate used in the present invention is a compound in which the conjugate (CDE) of cyclodextrin (CyD) and a polyamide amine dendrimer is modified with lactose.

The cyclodextrin constituting the cyclodextrin-polyamide amine dendrimer conjugate may be any of α, β or γ-cyclodextrin, and these α, β or γ-cyclodextrins include any of chemically modified or unmodified cyclodextrins. Common methods for chemically modifying cyclodextrin include, for example, methylation, hydroxyalkylation with such as hydroxyethyl or hydroxypropyl, glucosylation, maltosylation, alkylation, acylation, acetylation, sulfation, sulfobutylation, carboxymethylation, carboxyethylation, amination, carboxylation, tosylation, dimethylacetylation and the like. The chemically modified cyclodextrin can be any chemically modified cyclodextrin as long as there is no problem of toxicity or the like when administered to a living body, and examples thereof include the chemically modified α, β or γ-cyclodextrins described above, and it is preferably β-cyclodextrin, hydroxyalkyl-β-cyclodextrin or glucuronyl glucosyl-β-cyclodextrin (GUG-β-CyD), and further preferably hydroxypropyl-β-cyclodextrin or GUG-β-CyD.

The dendrimer/cyclodextrin conjugate that constitutes a part of the lactose-modified dendrimer/cyclodextrin conjugate used in the present invention is preferably a conjugate of glucuronyl glucosyl-β-cyclodextrin and a polyamide amine dendrimer (GUG-β-CDE). The polyamide amine dendrimer is a dendrimer having an alkylenediamine as a core, and the core alkylenediamine is not particularly limited, and examples thereof include dendrimers using commonly used types.

In the present specification, the lactose-modified cyclodextrin or a derivative thereof means lactose-modified chemically modified or unmodified α, β or γ-cyclodextrins or any of the cyclodextrins bound to a dendrimer. Modifications of lactose in the lactose-modified dendrimer/cyclodextrin include any of those in which the cyclodextrin molecule is modified with lactose, those in which the dendrimer molecule is modified with lactose, or those in which both the cyclodextrin molecule and the dendrimer molecule are modified with lactose.

Hereinafter, it will be described that a conjugate (GUG-β-CDE) of glucuronyl glucosyl-β-cyclodextrin (GUG-β-CyD) and a polyamide amine dendrimer having an alkylenediamine as a core (hereinafter, may be simply referred to as "dendrimer") as an example, but the present invention is not limited to this.

The conjugate (GUG-β-CDE) of glucuronyl glucosyl-β-cyclodextrin (GUG-β-CyD) and a polyamide amine dendrimer having an alkylenediamine as a core can be obtained by binding any GUG-β-CyD and any dendrimer according to a conventional method. 6-O-α-(4-O-α-D-glucuronyl)-D-glycosyl-β-cyclodextrin can be exemplified as GUG-β-CyD, but is not limited to this. The dendrimer includes, but not limited to, for example, the 2nd to 10th generation, preferably the 2nd to 6th generation, more preferably the 2nd or 3rd generation, and further preferably the 3rd generation dendrimers. The degree of substitution (DS) of cyclodextrin in GUG-β-CDE is 1 to 10, preferably 2 to 8, more preferably 2 to 6, and further preferably 3.

The conjugate of GUG-β-CyD and a dendrimer preferably used in the present invention is a conjugate of 6-O-α-(4-O-α-D-glucuronyl)-D-glycosyl-β-cyclodextrin and a third-generation dendrimer. Specific examples thereof include, but not limited to, GUG-β-CDE (G3, DS3), GUG-β-CDE (G3, DS4), GUG-β-CDE (G2, DS3), or GUG-β-CDE (G4, DS3).

Substitution of lactose in the dendrimer/cyclodextrin conjugate can be carried out with reference to known reports. In lactose-modification, a cyclodextrin can be modified, and a dendrimer can also be modified. For example, the lactose-modified dendrimer/cyclodextrin conjugate can be fabricated by any of a method of reacting a lactose-modified cyclodextrin and a dendrimer, a method of reacting a cyclodextrin and a lactose-modified dendrimer, or a method of modifying a dendrimer/cyclodextrin directly with lactose, but the method is not limited to them, and the method of reacting a lactose-modified cyclodextrin and a dendrimer is preferable. For example, lactose-modification can be easily performed on highly reactive functional groups such as an amino group, a carboxyl group, a hydroxyl group and the like present in cyclodextrins or dendrimers. The lactose-modification of cyclodextrin can be carried out with reference to known reports, but not limited to, the above described method can be used. For example, the lactose-modification of dendrimer can be conducted by using sodium cyanoborohydride (NaBH$_3$CN) and performing a reductive amination reaction between an amino group of a polyamide amine dendrimer and a hydroxyl group at the 1-position of lactose, but the method is not limited to this.

The degree of substitution of lactose in the lactose-modified dendrimer/cyclodextrin conjugate is not particularly limited. For example, when the cyclodextrin moiety is modified with lactose, the degree of substitution of lactose against cyclodextrin is not particularly limited, but is at least 1 or more, preferably 2 to 8, and further preferably 3 to 7, and when the dendrimer moiety is modified with lactose, the degree of substitution of lactose against dendrimer is not particularly limited, but is at least 1 or more, preferably 2 to 8, and further preferably 3 to 7. When the cyclodextrin and the dendrimer are randomly modified with lactose, the degree of substitution of lactose against one molecule of the dendrimer/cyclodextrin conjugate is not particularly limited, but at least 1 or more, preferably 2 or more, more preferably 3 or more, and further preferably 5 or more.

The lactose-modified dendrimer/cyclodextrin conjugate can also be modified with PEG or the like, which is also included in the lactose-modified cyclodextrin derivative of the present invention. Modification with PEG can be performed by binding PEG to the dendrimer using a known method. By modifying with PEG, an improvement of the blood retention can be expected.

(3) Drugs

The drug that can be used in the present invention includes, but is not limited to, for example, molecules that are substances in which the molecule itself exerts a physiological activity in the brain (hereinafter, may be simply referred to as a physiologically active substance) or substances exerting a function in the brain (hereinafter, may be simply referred to as intracerebral functional substance) (hereinafter, these may be collectively referred to as intracerebral active substances).

The physiologically active substance includes, but is not limited to, for example, low molecular weight compounds, polypeptides, oligopeptides, proteins and nucleic acids.

The low molecular weight compound includes, but is not limited to, compounds contained as an active ingredient in pharmaceuticals used for the treatment and/or prevention of various diseases related to the brain and the central nerve, for example, active ingredients of central nerve disease therapeutic agents, or compounds used for the treatment and/or prevention of brain diseases, for example, compounds having an anti-inflammatory action for suppressing inflammation in the brain, compounds exhibiting an anti-cancer action, compounds that are active ingredients of antibacterial agents and antiviral agents for the treatment of intracerebral infections, and the like.

Using a known method, complexes composed of these low molecular weight compounds and the lactose-modified cyclodextrin or lactose-modified dendrimer/cyclodextrin conjugate described above (hereinafter, these are collectively referred to as lactose-modified cyclodextrin or a derivative thereof) can be formed. Preferably, the low molecular weight compound is encapsulated in a lactose-modified cyclodextrin or a derivative thereof. Such complexes are also a part of the present invention.

Examples of the peptides (polypeptides and oligopeptides) include physiologically active peptides, and peptides used for the treatment and/or prevention of diseases related to the brain and central nervous system. Specific examples thereof include, but not limited to, somatostatin, which regulates the expression of enzymes involved in the degradation of amyloid beta peptide in the brain, insulin, which controls the function of nerve cells in the brain, or other peptides related to the function of the brain and central nervous system, and their derivatives.

Complexes composed of these peptides and the lactose-modified cyclodextrin or a derivative thereof of the present invention can be formed by using a known method. Examples thereof include, but not limited to, the following methods. By mixing the peptide as the target molecule and the lactose-modified cyclodextrin or a derivative thereof of the present invention, the peptide can be encapsulated in cyclodextrin to form a complex. Further, the peptide and/or the lactose-modified cyclodextrin or a derivative thereof of the present invention may be chemically modified, and then the two may be bound to each other, and in some cases via a spacer. Such complexes are also a part of the present invention.

The nucleic acid includes nucleic acids used for the treatment and/or prevention of diseases related to the brain and the central nervous system. Examples thereof include, but are not limited to, nucleic acids for the treatment of various diseases by gene knockdown method or using RNA interference, such as antisense nucleic acids (DNA and RNA), heteroduplex nucleic acids, siRNA and shRNA. Specific examples thereof include, but are not limited to, gene therapies for amyotrophic lateral sclerosis (ALS) and Parkinson's disease.

Complexes composed of these nucleic acids and the lactose-modified cyclodextrin or a derivative thereof of the present invention can be formed by using a known method. Examples thereof include, but are not limited to, the following methods. By mixing the nucleic acid as the target molecule and the lactose-modified cyclodextrin or a derivative thereof of the present invention, the nucleic acid can be encapsulated in the cyclodextrin to form a complex. Such complexes are also a part of the present invention.

The protein includes, but is not limited to, protein molecules having physiological activity in the brain, and proteins used for the treatment and/or prevention of diseases. Examples thereof include enzymes, antibodies, transcription factors, or specific parts constituting them.

Complexes composed of these proteins and the lactose-modified cyclodextrin or a derivative thereof of the present invention can be formed by using a known method. For example, the protein and/or the lactose-modified cyclodextrin or a derivative thereof of the present invention may be chemically modified, and then the two may be bound, and in some cases via a spacer, but the method is not limited to this. Alternatively, the protein and the lactose-modified cyclodextrin or a derivative thereof of the present invention may be bound in a non-covalent manner, for example electrostatically. Such complexes are also a part of the present invention.

The drug that can be preferably used as the physiologically active substance includes, but is not limited to, for example, anticancer agents, antiparkinson's disease agents, antidementia agents, and psychotropic agents. Since the lactose-modified cyclodextrin or a derivative thereof of the present invention promotes the permeation of a molecule that does not permeate the blood-brain barrier or has low permeability, a complex composed of a molecule that exhibits a more effective medicinal effect based on the promotion of absorption into the brain and the lactose-modified cyclodextrin or a derivative thereof of the present invention can be formed, and a pharmaceutical composition containing the complex can be provided.

The substance that exerts a function in the brain is a molecule that exerts a function other than physiological activity in the brain. Examples thereof include a molecule that serves as a marker in the brain, and a molecule that can be used for imaging a brain or a target in the brain (referred to as an intracerebral imaging molecule in the present specification). Examples thereof include, but are not limited to, compounds capable of visualizing targets in vivo, such as fluorescent dyes, quantum dots, nanomagnetic substances, nanogolds, intracellular molecule visualization reagents, and labeled molecules that can be detected by PET, and the like.

Complexes composed of these substances and the lactose-modified cyclodextrin or a derivative thereof of the present invention can be formed by using a known method, and a pharmaceutical composition containing the complex can be provided.

The lactose-modified cyclodextrin or a derivative thereof of the present invention can increase the blood-brain barrier permeability of a drug, and as a result, the drug can be delivered into the brain, thus, a substance having physiological activity in the brain or a substance exerting a function in the brain can be delivered into the brain, but the effect is not limited to this.

(4) Carrier for Drug Delivery

Since the lactose-modified cyclodextrin or a derivative thereof of the present invention can form a complex with a drug, permeate the blood-brain barrier, and carry the drug into the brain, it is also a carrier for delivering the drug to the brain. When the lactose-modified cyclodextrin or a derivative thereof of the present invention is used as a carrier for drug delivery into the brain, the type of cyclodextrin, the type of dendrimer, the degree of substitution of lactose and the like can be appropriately selected depending on the drug intended for delivery into the brain, and depending on the delivery purpose, for example, various conditions such as of delivery rate, delivery amount and the like.

Various carriers have been reported to deliver molecules into the brain. Examples thereof include, but are not limited to, liposomes, nanocarriers, exosomes, micelles or microcapsules. Reports on these carriers can also be used as a reference in determining the conditions under which the lactose-modified cyclodextrin or a derivative thereof of the present invention is used as a carrier for drug delivery to the brain.

(5) Brain-Penetrating Ligand

The following theories can be considered, though not bound by these theories. It is considered that the lactose-modified cyclodextrin or a derivative thereof of the present invention is taken up into the cell via a lactose-recognizing receptor or transporter present in cerebrovascular endothelial cells. In addition, the uptake of the lactose-modified cyclodextrin or a derivative thereof of the present invention into cerebrovascular endothelial cells is considered to be mediated by endocytosis. Therefore, the lactose-modified cyclodextrin or a derivative thereof of the present invention is also a brain-penetrating ligand.

As described above, the lactose-modified cyclodextrin or a derivative thereof of the present invention can deliver a substance having physiological activity in the brain or a substance exerting a function in the brain into the brain, but itself has a property of penetrating into the brain, therefore, the lactose-modified cyclodextrin or a derivative thereof of the present invention itself can also be utilized as a molecule penetrating into the brain, for example, by labeling it (for example, with a radionuclide for PET, a fluorescent dye, etc.).

The lactose-modified cyclodextrin or a derivative thereof of the present invention has cyclodextrin as a part thereof and can encapsulate a molecule to be delivered into the brain, and thus is excellent as a carrier for delivery into the brain or a brain-penetrating ligand.

A complex containing the lactose-modified cyclodextrin or a derivative thereof of the present invention and a drug can be used as a pharmaceutical composition. The pharmaceutical composition comprising the complex of the present invention can be formulated and administered according to known methods. For example, it can be administered parenterally or orally to mammals including humans as it is as a liquid preparation or as a pharmaceutical composition in a suitable dosage form. Examples of the parenteral administration method include injections and patches (transdermal administration). The pharmaceutical composition comprising the complex of the present invention is preferably administered parenterally.

The pharmaceutical composition comprising the complex of the present invention may appropriately contain any component as long as the effects of the drug and the lactose-modified cyclodextrin or a derivative thereof of the present invention are not impaired. Optional ingredients include, but are not limited to, cross-linking agents, solubilizers, emulsifiers, moisturizers, refreshing agents, inorganic powders, antioxidants, preservatives, coloring agents, flavoring agents, pH adjusters and stabilizers.

The pharmaceutical composition of the present invention can be used as a pharmaceutical composition for preventing or treating a cranial nerve system disease or disorder. The cranial nerve system disease or disorder includes, but is not limited to, for example, Alzheimer's disease, malignant brain tumor, Parkinson's disease, Niemann-Pick disease type C, cerebral stroke, cerebral ischemia, dementia, muscular dystrophy, multiple sclerosis, amyotrophic lateral sclerosis, cystic fibrosis, Angelman's syndrome, Riddle Syndrome, myasthenia gravis, spinal muscle atrophy, Down's syndrome, Huntington's disease, schizophrenia, depression, Tauopathy disease, Pick's disease, Paget's disease, lysosome disease accompanied by brain damage, cancer, prion's disease, traumatic brain injury, and viral or bacterial central nervous system disorders, and the like.

The dose of the complex composed of the lactose-modified cyclodextrin or a derivative thereof of the present invention and a drug to human is appropriately determined depending on the type of the active substance contained, the age, body weight, condition and sex of the subject to be administered, the administration method, and other conditions. For example, the dose of the active substance may be about 0.01 mg/kg to about 10 mg/kg per day.

EXAMPLES

Hereinafter, the present invention will be specifically described with reference to examples, but the present invention is not limited to the following examples.

(Example 1) Production of Lactose-Modified Cyclodextrin

Using $\beta$-cyclodextrin as cyclodextrin, a lactose-modified cyclodextrin (Lac-$\beta$-CyD) was produced as follows.

Figure 3:
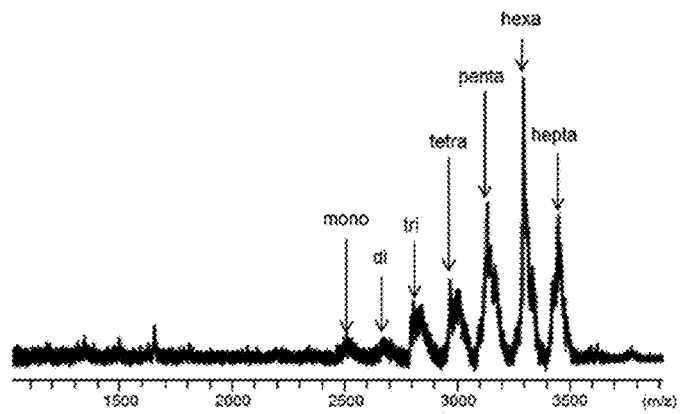
FIG. 3 shows the results of measuring the MALDI-TOF MS spectrum of Lac-β-CyD produced in Example 1.
Figure 4:
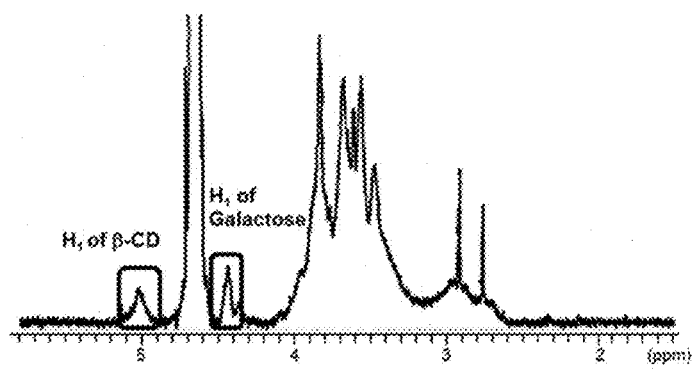
FIG. 4 shows the results of measuring the $^1$H-NMR spectrum of Lac-β-CyD produced in Example 1.

It was produced by a step shown in FIG. 2 in accordance with the description of Non-Patent Document 4 (Motoyama et al., Beilstein J Org. Chem. 13, 10-18, 2017). The yield of Lac-$\beta$-CyD was 25%. As a result of measuring the MALDI-TOF MS spectrum of Lac-$\beta$-CyD, the presence of tri-, tetra-, penta-, hexa-, and hepta-lactose-substituted $\beta$-CyD was confirmed as shown in FIG. 3. The results of measuring the $^1$H-NMR spectrum of Lac-$\beta$-CyD are shown in FIG. 4. The degree of substitution of lactose (DSL) of Lac-$\beta$-CyD was 5.6.

(Example 2) Preparation of Lactose-Modified Dendrimer/Glucuronyl Glucosyl-Cyclodextrin (Lac-GUG-$\beta$-CyD)

Figure 5:
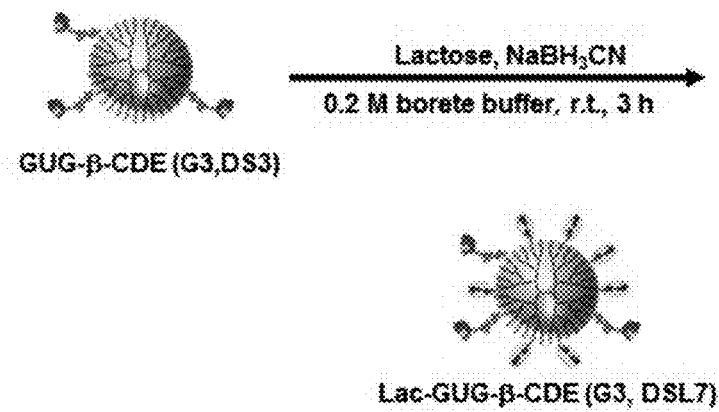
FIG. 5 shows an example of the synthesis of a lactose-modified dendrimer/glucuronyl-β-cyclodextrin (Lac-GUG-β-CyD).

Using dendrimer/glucuronyl-$\beta$-cyclodextrin (GUG-3-CDE: G3, DS3) as the dendrimer/glucuronyl cyclodextrin, lactose-modification was performed as follows. The outline is shown in FIG. 5.

(2-1) Preparation of GUG-$\beta$-CDE (G3)

1.5 mL of dendrimer (G3) was added to a test tube and evaporated. 95.9 mg of GUG-$\beta$-CyD and 22.0 mg of DMT-MM were dissolved in 0.5 mL of DMSO and the solution was added to the test tube. Then, after reacting at room temperature for 12 hours, dialysis (dialysis membrane: MWCO=3,500) was performed for 7 days, then, the preparation was confirmed by TCL (developing solvent: 1-butanol/ethanol/water=5:4:3 (v/v/v), coloring reagent: anisaldehyde), and the liquid was evaporated. After washing with excess ethanol under ice cooling, the precipitate was dissolved in distilled water. After freeze-drying, this product was obtained.

(2-2) Preparation of Lac-GUG-β-CyD (G3)

Figure 6:
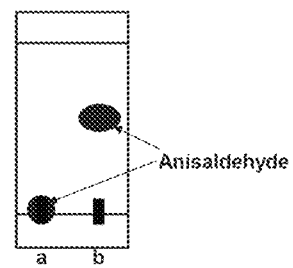
FIG. 6 shows the results of developing Lac-GUG-β-CDE produced in Example 2 by thin layer chromatography with a developing solvent of 1-butanol/ethanol/water=5/4/3. As the color former, p-anisaldehyde was used. Lactose was used as the control.

78.7 mg of GUG-β-CDE, 20.3 mg of Lactose-hydrate and 7.0 mg of sodium cyanoborohydride were added to a test tube and dissolved with 2.0 mL of 0.2 M borate buffer (pH 7.5). Then, after reacting at room temperature for 3 hours, dialysis was performed for 2 days (dialysis membrane: MWCO=3,500), then, the preparation was confirmed by TCL (developing solvent: 1-butanol/ethanol/water=5:4:3 (v/v/v), coloring reagent: anisaldehyde) (FIG. 6), and the liquid was evaporated. After washing with excess ethanol under ice cooling, the precipitate was dissolved in distilled water. After freeze-drying, this product was obtained.

Figure 7:
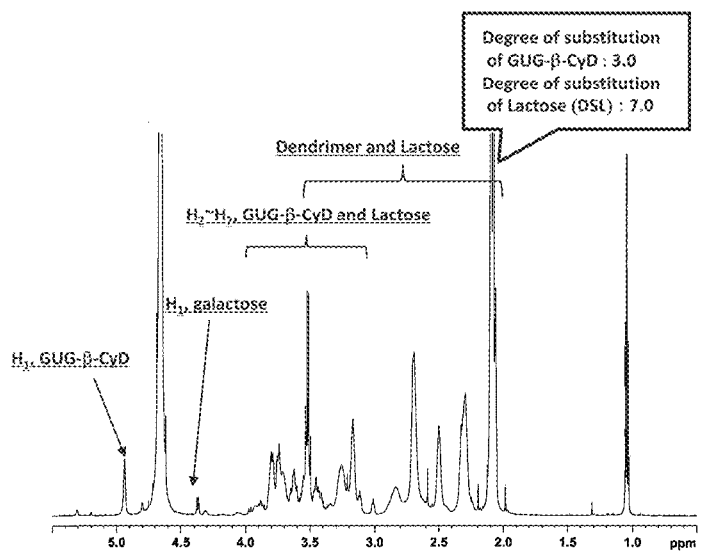
FIG. 7 shows the results of measuring the $^1$H-NMR spectrum of Lac-GUG-β-CDE produced in Example 2.

Then, the $^1$H-NMR spectrum of the produced Lac-GUG-β-CDE was measured. The results are shown in FIG. 7. The degree of substitution of GUG-β-CyD against one molecule of dendrimer was 3.0, and the degree of substitution of lactose (DSL) was 7.0.

(Example 3) Confirmation of Brain Penetrating Property

The lactose-modified-cyclodextrin produced in Example 1 was labeled with Cy5 as follows. 20 mg of Lac-β-CyD and 1 mg of Cy5 mono NHS ester were dissolved in 1 mL of Milli-Q and reacted at room temperature in the dark for 18 hours. Then, after dialysis in water for 48 hours (dialysis membrane (Spectra/Pore) MWCO: 1,000), the preparation was confirmed by TCL (developing solvent: 1-butanol/ethanol/water=5:4:3 (v/v/v)), coloring reagent: anisaldehyde), and after freeze-drying, Cy5-labeled Lac-β-CyD was obtained.

Figure 8:
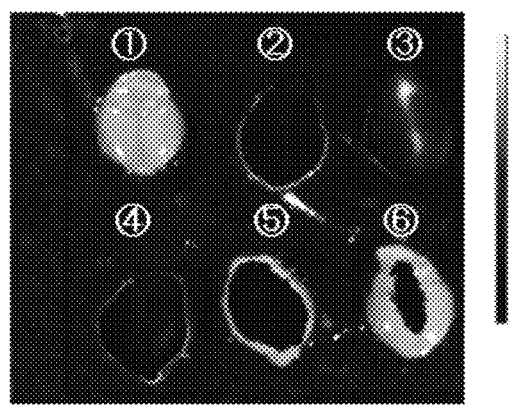
FIG. 8 shows the results obtained by subcutaneously administering Cy5-Lac-β-CyD (DSL5.6) in mice, and then collecting the brain 5, 10, 30, 60 and 180 minutes later and detecting using an IVIS imaging system. The figure shows typical images of three experiments.

The labeled Cy5-Lac-β-CyD (DSL5.6) dissolved in physiological saline was subcutaneously injected into each BALB/c mouse (8 weeks old, male, 20 g) so as to be 20 mg/kg. Controls were injected with physiological saline. Mice were euthanized, and perfused with PBS and the brain was removed 0, 5, 10, 30, 60, and 180 minutes after administration. The removed brain was observed in an in vitro image spectrum (IVIS) (Ex: 535 nm, Em: DsRed). The results are shown in FIG. 8. The brain collected 10 minutes after administration showed the strongest fluorescence.

(Example 4) Confirmation of Permeability of Lac-GUG-β-CDE in in Vitro Blood-Brain Barrier Model Using an in vitro blood-brain barrier model, the time-dependent permeation amount of Lac-GUG-β-CDE was evaluated as follows.

Figure 9:
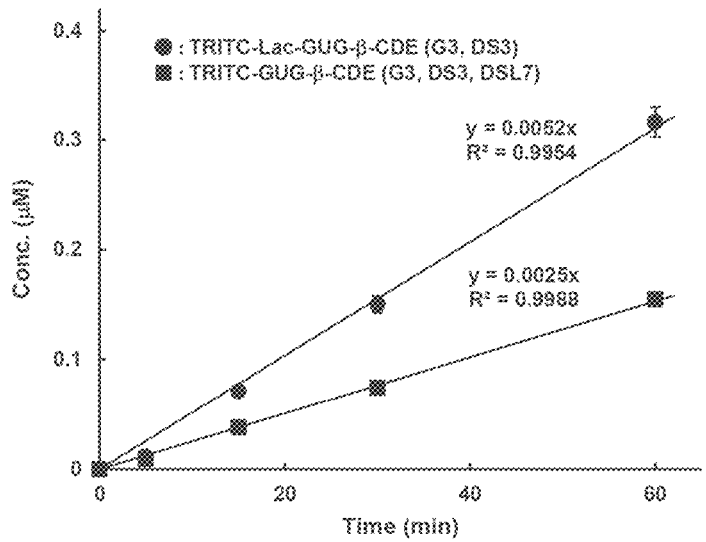
FIG. 9 shows the results of measuring the permeation amount of TRITC-GUG-β-CUE (G3, DS3) and TRITC-Lac-GUG-β-CDE (G3, DS3, DSL7) using the hCMEC/D3 cell monolayer. Each value shows the average of 4 experiments±S. E.

First, Lac-GUG-β-CDE and the control GUG-β-CDE were labeled with TRITC as follows. 10 mg of GUG-β-CDE (G3, DS3) and 1 mg of TRITC were dissolved in 1 mL of DMSO and reacted at room temperature in the dark for 24 hours. Then, after 48 hours of dialysis in water (dialysis membrane (Spectra/Pore) MWCO: 3,500), preparation was confirmed by TCL (developing solvent: 1-butanol/ethanol/water=5:4:3 (v/v/v), coloring reagent: anisaldehyde), and after freeze-drying, TRITC-labeled GUG-β-CDE (G3, DS3) was obtained.

hCMEC/D3 cells were seeded in transwells at $1.0\times10^5$ cells/well, and cultured at 37° C. in a $CO_2$ incubator for 4 to 6 days. Prior to the start of the experiment, hCMEC/D3 cell monolayers were equilibrated in EBM-2 medium (37° C., 1.5 mL on the apical side, 2.6 mL on the basal side). TRITC-GUG-β-CDE (G3, DS3) or TRITC-Lac-GUG-β-CDE (G3, DS3, DSL7) was dissolved in EBM-2 medium to a concentration of 10 μM, respectively, and replaced with the medium on the apical side. After 5, 15, 30, and 60 minutes, TRITC-GUG-β-CDE or TRITC-Lac-GUG-β-CDE in EMB-2 medium on the basal side was measured. The results are shown in FIG. 9. Moreover, each permeation coefficient was as follows.

TABLE 1

| $P_{app}$ to TRITC-Lac-GUG-β-CDE (G3, DS3, DSL7) of hCMEC/D3 Cell Monolayers | | |
|---|---|---|
| | TRITC-GUG-β-CDE (G3, DS3) | TRITC-Lac-GUG-β-CDE (G3, DS3, DSL7) |
| $P_{app}$ ($\times10^{-4}$ cm/min) | 1.4 ± 0.056 | 2.9 ± 0.130 * |

Each value shows the average of 4 experiments ± S.E.
* indicates p < 0.05 when compared with TRITC-GUG-β-CDE.

(Example 5) Evaluation of Influence on Tight Junction of Blood-Brain Barrier

Figure 10:
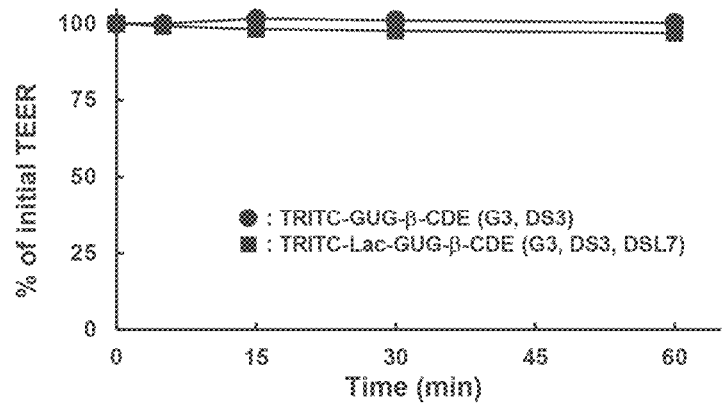
FIG. 10 shows the results of confirming the influence of TRITC-GUG-β-CDE (G3, DS3) and TRITC-Lac-GUG-β-CDE (G3, DS3, DSL7) on the tight junction of the hCMEC/D3 cell monolayer. Each value shows the average of 4 experiments±S. E.

The influences of TRITC-GUG-β-CDE (G3, DS3) and TRITC-Lac-GUG-β-CDE (G3, DS3, DSL7) on the tight junction of the blood-brain barrier were examined as follows.

hCMEC/D3 cells were seeded in transwells at $1.0\times10^5$ cells/well, and cultured at 37° C. in a $CO_2$ incubator for 4 to 6 days. Prior to the start of the experiment, hCMEC/D3 cell monolayers were equilibrated in EBM-2 medium (37° C., 2.0 mL on the apical side, 2.0 mL on the basal side). TRITC-GUG-β-CDE (G3, DS3) or TRITC-Lac-GUG-β-CDE (G3, DS3, DSL7) was dissolved in EBM-2 medium to a concentration of 10 μM, respectively, and after warming to 37° C. previously, the resultant medium was replaced with the medium on the apical side. After 5, 15, 30, and 60 minutes, the influence on the tight junction was evaluated by measuring the trans-epithelial electrical resistance (TEER) of the monolayer. As shown in FIG. 10, neither TRITC-GUG-β-CDE nor TRITC-Lac-GUG-β-CDE reduced the tight junction of the cells. Therefore, it was suggested that it does not cause cell damage at the blood-brain barrier.

(Example 6) Evaluation of Endocytosis

Figure 11:
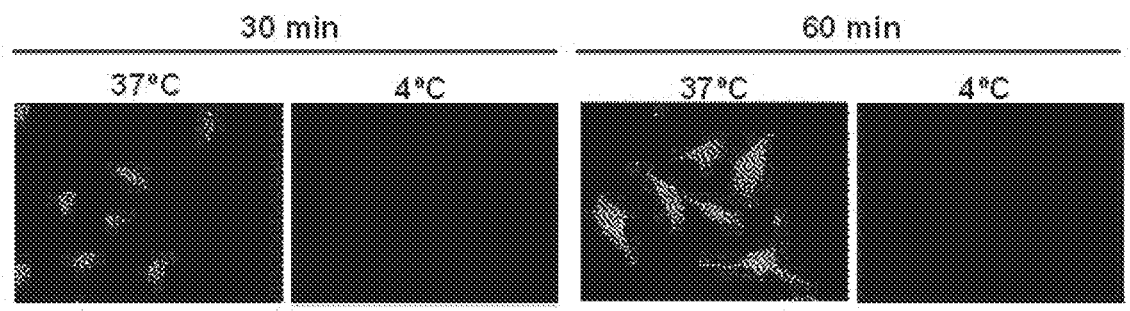
FIG. 11 shows the results of observing cells with a fluorescence microscope, after treating hCMEC/D3 cells with TRITC-Lac-GUG-β-CDE (G3, DS3, DSL7) for 30 and 60 minutes at 4° C. or 37° C. The figure shows typical images at three points.
Figure 12:
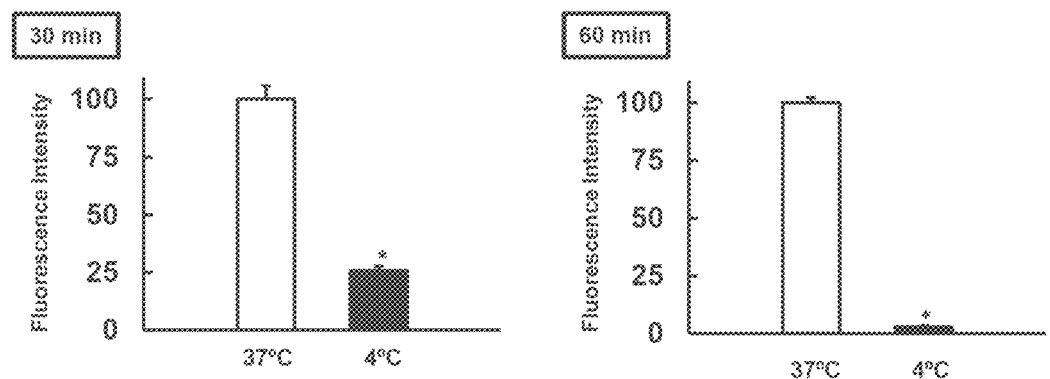
FIG. 12 shows the result of numerically expressing the fluorescence intensity in the observation of FIG. 11. Each value shows the average of 3 observations±S. E. * indicates $p<0.05$ when compared with 37° C.

It was confirmed as follows whether the intracellular uptake of TRITC-Lac-GUG-β-CDE (G3, DS3, DSL7) is caused by endocytosis.

hCMEC/D3 cells ($1.0\times10^4$ cells/well) were treated with TRITC-Lac-GUG-β-CDE (G3, DS3, DSL7) for 30 and 60 minutes. The culture temperature used was 4° C. or 37° C. After washing the cells with PBS, the cells were observed with a fluorescence microscope. The results are shown in FIG. 11. Observations are made at three independent points, and the figure shows a representative image. The result of measuring the fluorescence intensity with the BZ-II analyzer is shown in FIG. 12. Since the uptake of TRITC-Lac-GUG-β-CDE did not occur at 4° C., it was found that TRITC-Lac-GUG-β-CDE was taken up into the cells through the endocytosis pathway.

(Example 7) Evaluation of Competitive Inhibition by Lactose

It was confirmed as follows whether or not the intracellular uptake of TRITC-Lac-GUG-β-CDE (G3, DS3, DSL7) was competitively inhibited by lactose.

Figure 13:
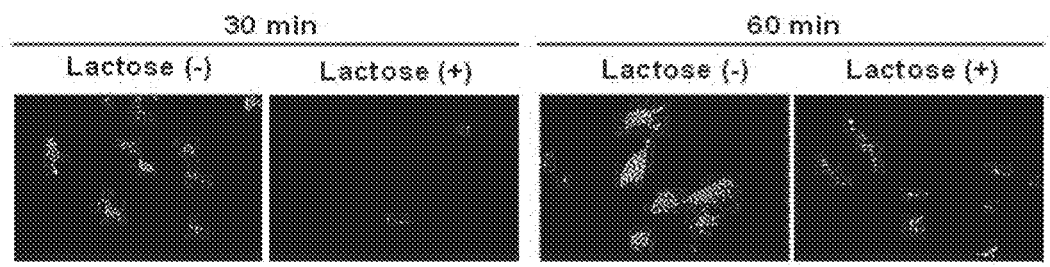
FIG. 13 shows the results of observing the competitive inhibition of lactose against the uptake of TRITC-Lac-GUG- β-CDE (G3, DS3, DSL7) in hCMEC/D3 cells with a fluorescence microscope. The figure shows typical images at three points.
Figure 14:
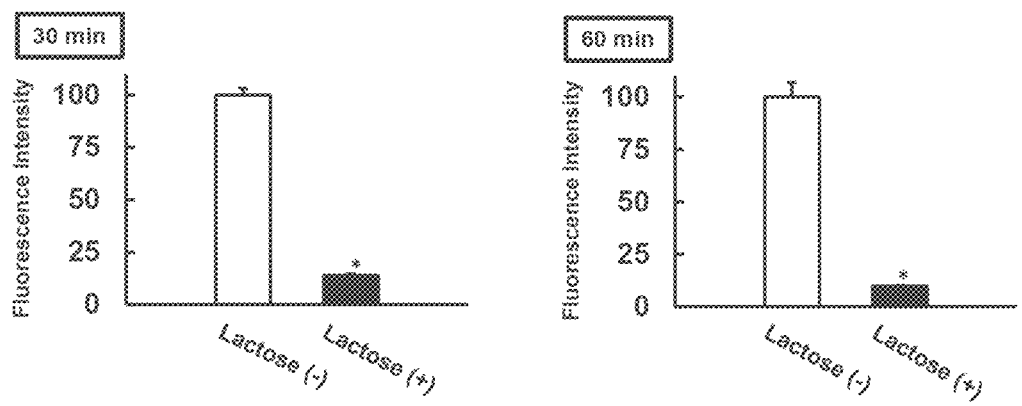
FIG. 14 shows the result of numerically expressing the fluorescence intensity in the observation of FIG. 13. Each value shows the average of 3 observations±S. E. * indicates p<0.05 when compared with the case where lactose is not added.

At a temperature of 37° C., hCMEC/D3 cells (1.0×10$^4$ cells/well) were treated with TRITC-Lac-GUG-β-CDE (G3, DS3, DSL7) for 30 minutes and 60 minutes, in the presence of lactose (4 mM). After washing the cells with PBS, the cells were observed with a fluorescence microscope. The results are shown in FIG. 13. Observations are made at three independent points, and the figure shows a representative image. The result of measuring the fluorescence intensity with the BZ-II analyzer is shown in FIG. 14. It was confirmed that the uptake of TRITC-Lac-GUG-β-CDE was competitively inhibited by lactose. This result suggests that the uptake of TRITC-Lac-GUG-β-CDE is mediated by a receptor that recognizes lactose.

(Example 8) Evaluation of Uptake into Neuroblasts

It was confirmed as follows whether or not TRITC-Lac-GUG-β-CDE (G3, DS3, DSL7) was taken up into neuroblasts.

Figure 15:
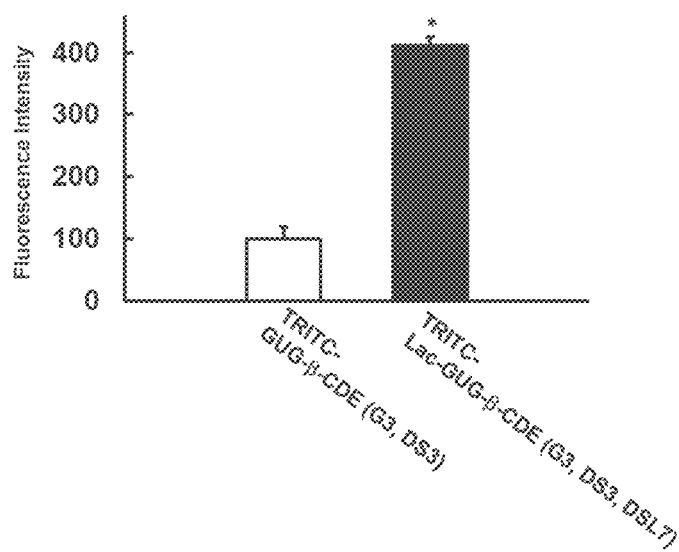
FIG. 15 shows the results of confirming the uptake of TRITC-GUG-β-CDE (G3, DS3) and TRITC-Lac-GUG-β-CDE (G3, DS3, DSL7) into nerve cells using SH-SY5Y cells. Each value shows the average of 3 experiments±S. E. * indicates p<0.05 when compared with TRITC-GUG-β-CDE.

SH-SY5Y cells (1.0×10$^4$ cells/well), which are human neuroblasts, were treated with TRITC-GUG-β-CDE (G3, DS3) and TRITC-Lac-GUG-β-CDE (G3, DS3, DSL7) for 60 minutes. The culture temperature used was 37° C. After washing the cells with PBS, the fluorescence intensity of the cells was measured with the BZ-II analyzer. The results are shown in FIG. 15. It was found that TRITC-Lac-GUG-β-CDE is also taken up by nerve cells.

(Example 9) Synthesis of Lactose-Modified Hydroxypropyl-β-Cyclodextrin

Hydroxypropyl-β-cyclodextrin was used as cyclodextrin, and a lactose-modified hydroxypropyl-β-cyclodextrin (Lac-HP-β-CyD) was synthesized as follows.

Figure 16:
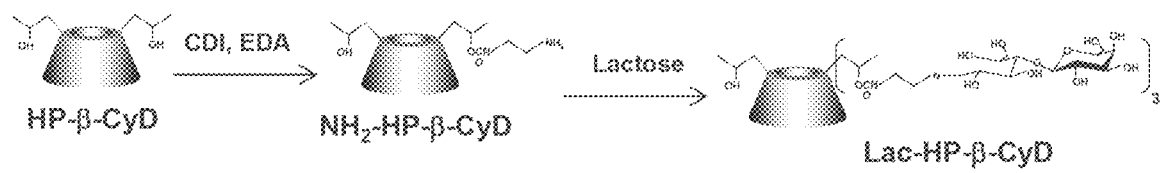
FIG. 16 shows an outline of the synthetic pathway of Lac-HP-β-cyclodextrin.
Figure 17:
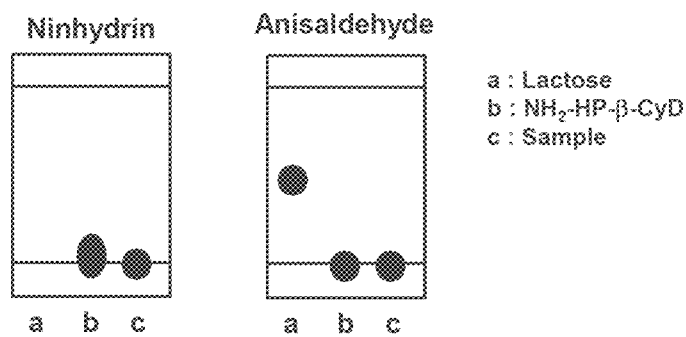
FIG. 17 shows the result of developing Lac-HP-β-CyD produced in Example 9 by thin layer chromatography with a developing solvent of ethanol/water=9/1. Ninhydrin and p-anisaldehyde were used as color formers. c is Lac-HP-β-CyD.
Figure 18:
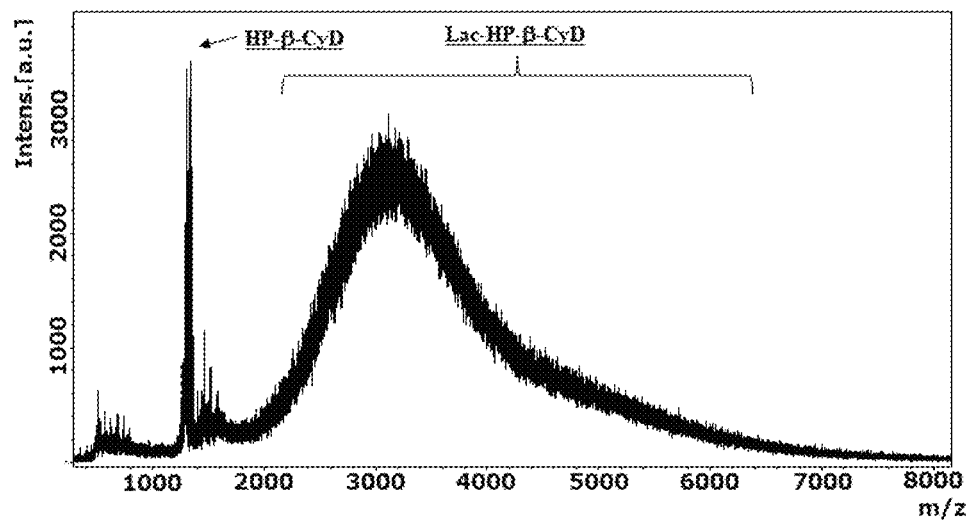
FIG. 18 shows the results of measuring the MALDI-TOF MS spectrum of Lac-HP-β-CyD produced in Example 9.
Figure 19:
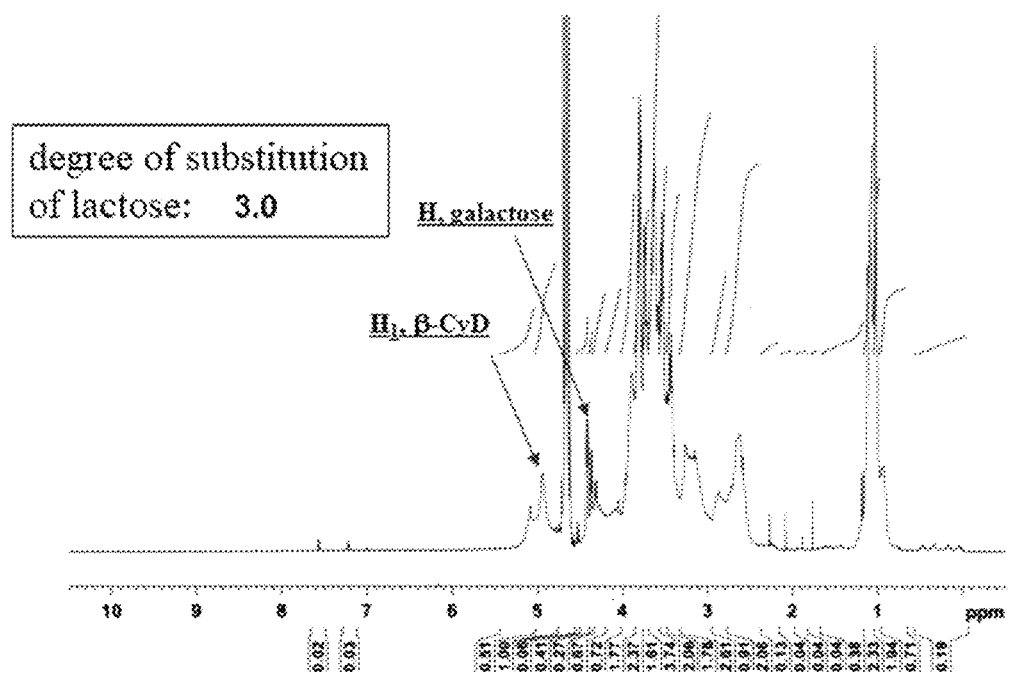
FIG. 19 shows the results of measuring the $^1$H-NMR spectrum of Lac-HP-β-CyD produced in Example 9.

The outline of the synthesis is shown in FIG. 16. 10.5 mL of ethylenediamine was added to 1.0 g of HP-β-CyD, and the reaction was carried out using CDI. 1.0 g of the obtained NH$_2$-HP-β-CyD (ethylenediamine) was dissolved in DMSO, and sodium cyanoborohydride (3.3 g) was added. Further, lactose monohydrate (18.3 g) was added, and the mixture was stirred at 75° C. for 48 hours. The lactose molar ratio to NH$_2$-HP-3-CyD is 1:100. After dialysis (dialysis membrane: MWCO=1,000 for 6 hours, MWCO=500 to 1,000 for 48 hours), preparation was confirmed by TCL (developing solvent: ethanol/water=9:1 (v/v), coloring reagent: ninhydrin or anisaldehyde) (FIG. 17), and after freeze-drying, this product was obtained. The MALDI-TOF MS spectrum and $^1$H-NMR spectrum of the obtained sample were measured. The results are shown in FIGS. 18 and 19. The degree of substitution of lactose was 3.0.

(Example 10) Influence of Lac-HP-β-CyD on Cholesterol Leakage

Figure 20:
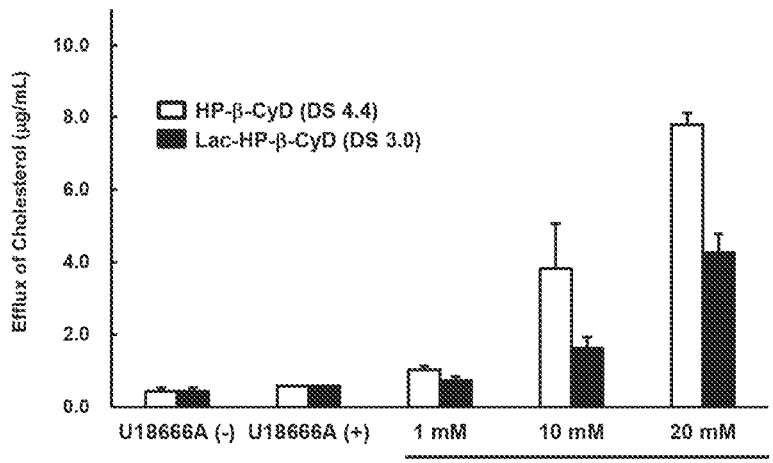
FIG. 20 shows the results of confirming the influence of Lac-HP-β-CyD on cholesterol leakage using SH-SY5Y cells. Each value shows the average of two experiments±S. E.

SH-SY5Y cells (1.0×10$^5$ cells), which are human neuroblasts, were seeded in a 24-well plate, incubated at 37° C. for 24 hours, then, washed with PBS, and a medium supplemented with U18666A (7.5 μM) was added, and it was incubated for an additional 24 hours. Then, washed with PBS, and 150 μL of a medium (HBSS, FBS (−)) containing HP-3-CyD (DS4.4) (1.0, 10.0 and 20.0 mM) or Lac-HP-β-CyD (DSL3.0) (1.0, 10.0 and 20.0 mM) was added. After incubating at 37° C. for 2 hours, the supernatant was collected and centrifuged (10,000). The cholesterol concentration and phospholipid concentration in the obtained supernatant were measured with cholesterol E-Test wako and phospholipid C-Test wako. The results are shown in FIG. 20. Lac-HP-β-CyD had less cholesterol leakage than HP-β-CyD.

(Example 11) Uptake of Lac-HP-β-CyD into hCMEC/D3 Cells

Lac-HP-β-CyD (DSL3.0) and the control HP-β-CyD (DS4.0) were labeled with HiLyte fluorescent dye according to the manufacturer's manual. The following experiments were carried out using these.

Figure 21:
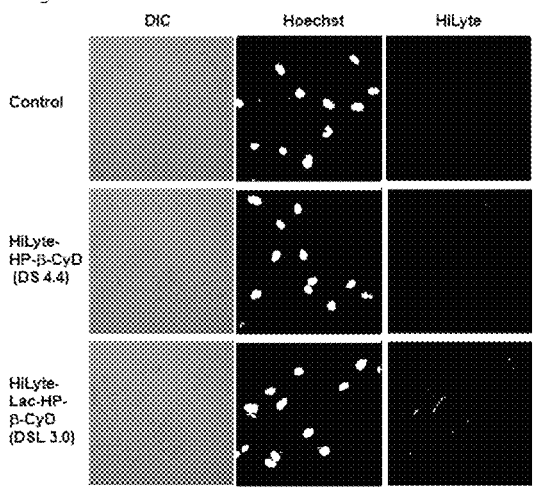
FIG. 21 shows the results of confirming the uptake of HiLyte-Lac-HP-β-CyD into hCMEC/D3 cells.

Using hCMEC/D3 cells, which are human brain capillary endothelial cells, the uptake of Lac-HP-β-CyD into cells was confirmed. hCMEC/D3 cells were seeded at 1.0×10$^4$ cells/ glass dish and incubated at 37° C. for 24 hours. Then, it was washed with PBS, and 150 μL of a medium containing HiLyte-HP-β-CyD (DS4.4, 1 mM) or HiLyte-Lac-HP-β-CyD (DSL3.0, 1 mM) was added, and incubated at 37° C. for 1 hour. After washing with PBS, it was fixed with 4% paraformaldehyde. After adding the Hoechst solution and incubating at 37° C. for 30 minutes, fluorescence was observed with a confocal microscope. The results are shown in FIG. 21. It was confirmed that Lac-HP-β-CyD was significantly taken up into the cells as compared with HP-β-CyD.

(Example 12) Evaluation of Influence on Membrane Permeability of Lac-HP-β-CyD

Figure 22:
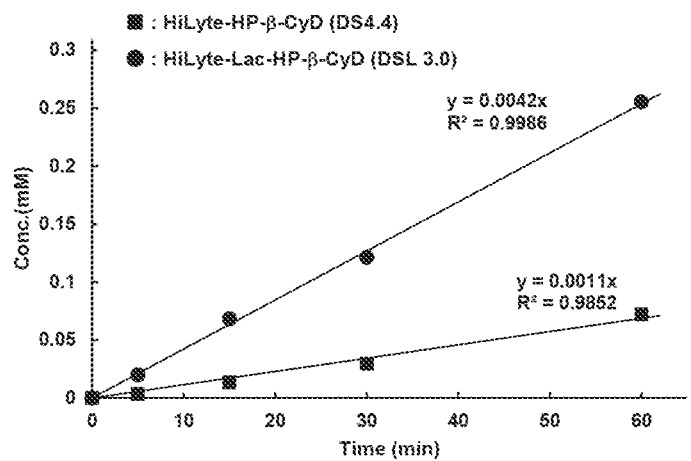
FIG. 22 shows the results of measuring the permeation amount of HiLyte-Lac-HP-β-CyD (DSL3.0) and HiLyte-HP-β-CyD (DS4.4) using the hCMEC/D3 cell monolayer. Each value shows the average of two experiments±S. E.

Using hCMEC/D3 cells and SH-SY5Y cells, the influence on membrane permeability of HiLyte-Lac-HP-β-CyD was measured.

hCMEC/D3 cells were seeded in the upper component of a transwell at 2.0×10$^5$ cells/well, incubated at 37° C. for 5 days, then, the transepithelial electrical resistance (TEER) was measured. SH-SY5Y cells were seeded at 1.0×10$^5$ cells/well in a 6-well plate, which is a lower component, and incubated at 37° C. for 1 day. Then, the media at the upper side and lower side were aspirated, and the EBM-2 medium containing HiLyte-HP-β-CyD (DS4.4, 1 mM) or HiLyte-Lac-HP-β-CyD (DSL3.0, 1 mM) was added to the upper side in an amount of 1.5 mL, and 2.6 mL of a medium containing no of them was added to the lower side. Over time (upper side 0, 60 minutes; lower side 0, 5, 15, 30, and 60 minutes), the medium was sampled, the fluorescence intensity was measured using I-control (M1000) (TECAN), and the permeation amount was measured. The result measuring the permeation to the lower side is shown in FIG. 22. Similar to Example 4, the permeation coefficient Papp (cm/sec) was calculated as follows.

Papp=(dQ/dt)/(A*Co)

Q: Permeation amount (mol), A: Cell surface area (cm$^2$), Co: Initial concentration (mol/mL)

TABLE 2

$P_{app}$ of HiLyte-Lac-HP-β-CyD (DSL 3.0) in hCMEC/D3 Cell Monolayers

| | $P_{app}$ (×10$^{-3}$ cm/min) |
|---|---|
| HiLyte-HP-β-CyD (DS 4.4) | 0.62 |
| HiLyte-Lac-HP-β-CyD (DSL 3.0) | 2.24 |

Each value shows the average of one experiment ± S.E.

Figure 23:
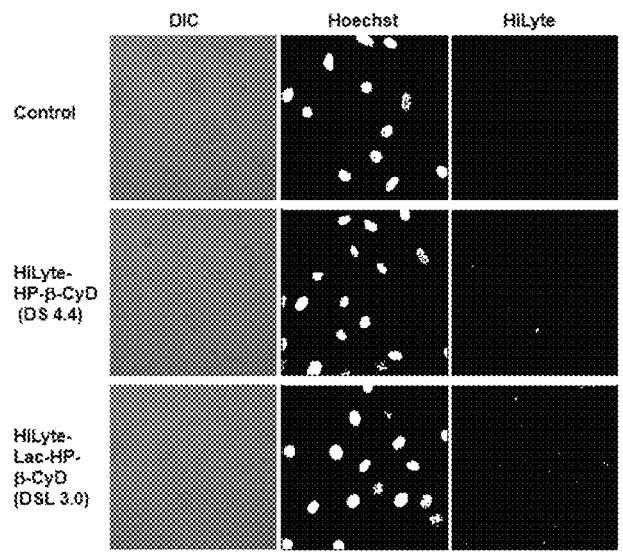
FIG. 23 shows the results of confirming the uptake of HiLyte-Lac-HP-β-CyD, which has permeated the hCMEC/D3 cell monolayer, into SH-SY5Y cells.

Further, at the time of 60 minutes, the lower side was washed with PBS and the fluorescence was observed with a confocal microscope. The results are shown in FIG. 23. From these results, it was confirmed that Lac-HP-β-CyD was significantly taken up into SH-SY5Y cells after BBB permeation as compared with HP-β-CyD.

(Example 13) Influence of Lac-HP-β-CyD on Intracellular Accumulation of Amyloid β

Figure 24:
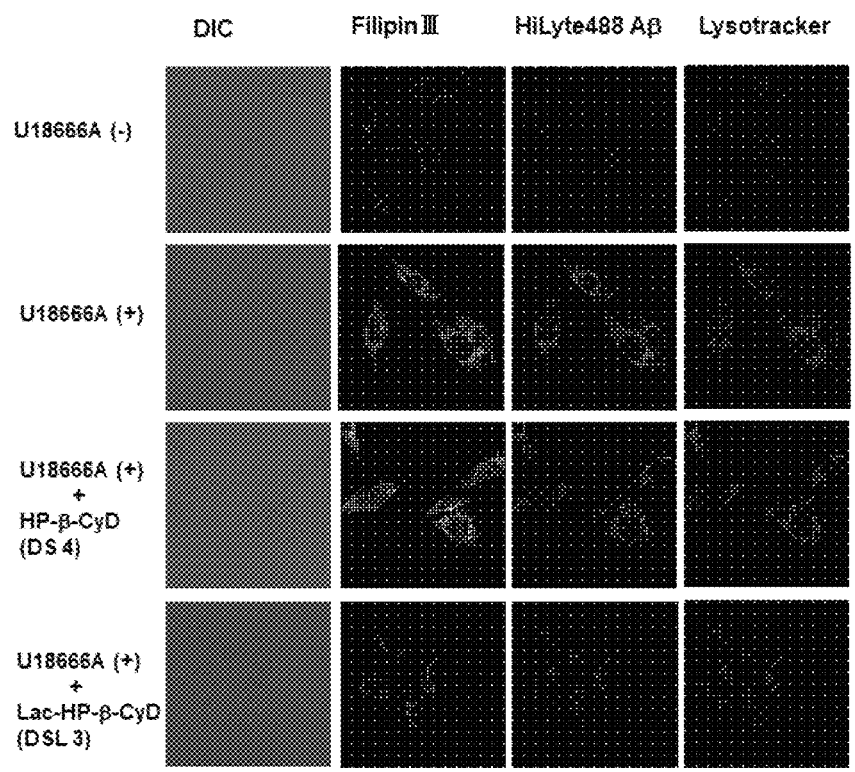
FIG. 24 shows the results of confirming the accumulation of amyloid Aβ in H-SY5Y cells and the influence of Lac-HP-β-CyD on it. The experiment was performed once each, and the figure shows a typical image.

Using SH-SY5Y cells, the amyloid β accumulation in the cells was measured. SH-SY5Y cells were seeded at $1.0 \times 10^4$ cells/glass dish and incubated at 37° C. for 24 hours. Then, washed with PBS, 150 µL of a medium containing U18666A (7.5 µM) and HiLyte488-Aβ (purchased from AnaSpec) (250 nM) was added and incubated at 37° C. for 24 hours. After washing with PBS, 200 µL of a medium containing HP-β-CyD (DS4.4.1 mM) or Lac-HP-β-CyD (DSL3.0, 1 mM) was added, and the mixture was incubated at 37° C. for 24 hours. After washing with PBS, 200 µL of a medium supplemented with Lysostacker (registered trademark) (final concentration: 100 nM) was added. After incubating for 30 minutes, it was fixed with 4% paraformaldehyde and the FIlipin solution was added. Incubation was performed at 37° C. for 1 hour, and the fluorescence was observed with a confocal microscope. The results are shown in FIG. 24. It was observed that Lac-HP-β-CyD normalized the Aβ clearance by reducing the amount of cholesterol in cells.

(Example 14) Organ Distribution of Fluorescently Labeled Lac-HP-β-CyD

Figure 25:
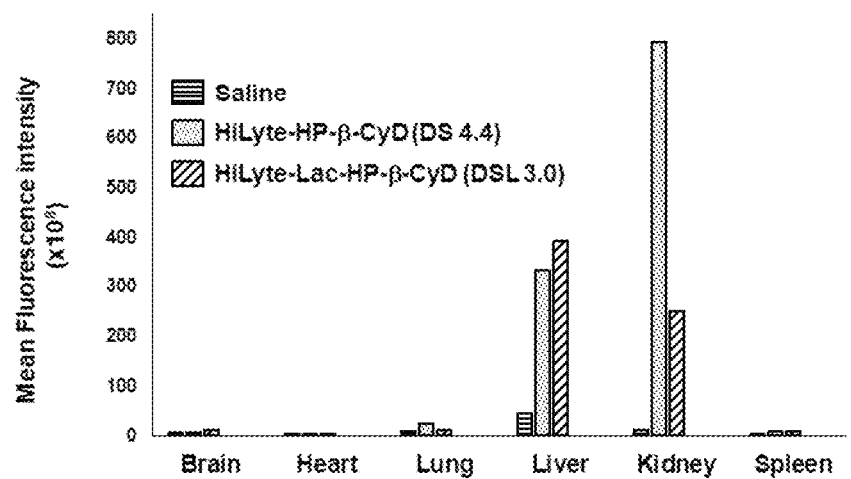
FIG. 25 shows the result of confirming the distribution of HiLyte-Lac-β-CyD intravenously injected into mice to each organ. Three experiments were performed. An example of the result is shown.
Figure 26:
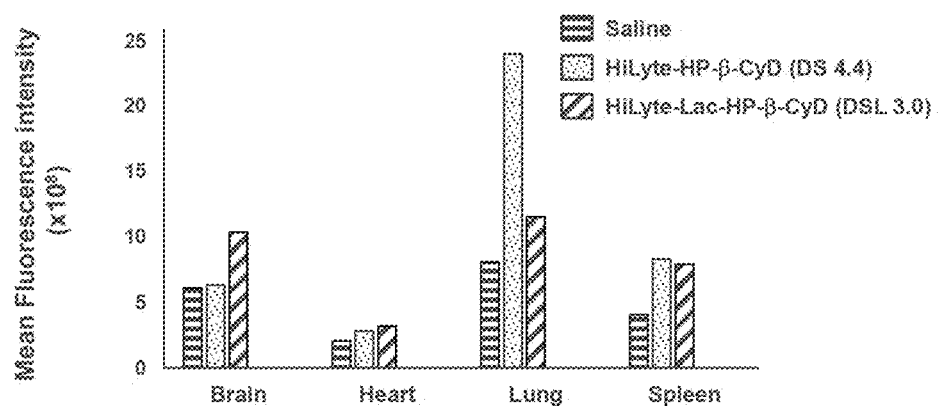
FIG. 26 is a view showing the results of penetration into the brain, the heart, the lung, and the spleen.
Figure 27:
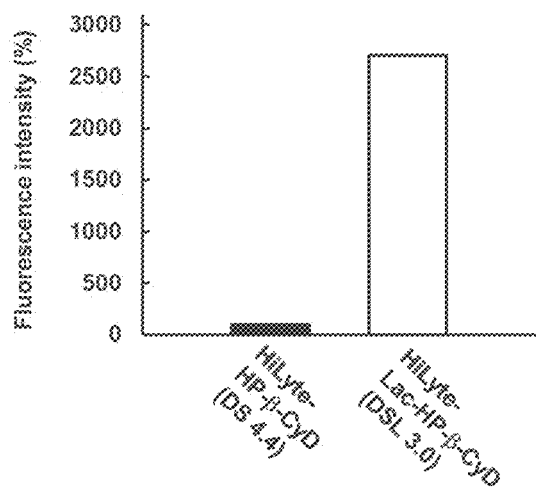
FIG. 27 is a view showing the result of penetration into the brain.

BALB/c mice (8 weeks old, male, 20 g) were intravenously injected with HiLyte-HP-β-CyD (DS4.4) or HiLyte-Lac-HP-β-CyD (DSL3.0) at a dose of 10 mg/kg. After 10 minutes, the mice were euthanized, perfused with PBS and each organ was collected. Each organ was observed by IVIS. The results of the fluorescence intensity of each organ are shown in FIG. 25. FIG. 26 shows the expanded results of the fluorescence intensity of the brain, the heart, the lung, and the spleen, which are organs with low uptake. Further, FIG. 27 shows the result when the uptake into the brain is expressed with the control as 100. From this result, it was confirmed that Lac-HP-β-CyD significantly penetrated to the brain as compared with HP-β-CyD.

The above-described detailed description merely illustrates objects and subjects of the present invention, and does not limit the accompanying Claims. Without departing from the accompanying Claims, various modifications and alterations to the described embodiments will be apparent to those skilled in the art in view of the teachings herein.

INDUSTRIAL APPLICABILITY

The lactose-modified cyclodextrin or dendrimer/glucuronyl glucosyl-cyclodextrin of the present invention permeates the blood-brain barrier, hence, it is useful as a carrier molecule for delivering a drug into the brain.

The invention claimed is:

1. A method for treating a neurological disease or disorder comprising administering a composition comprising (i) a lactose-modified cyclodextrin or a derivative thereof and (i) a drug encapsulated in the lactose-modified cyclodextrin or the derivative thereof to a patient in need of administration of the drug into a brain,
wherein the lactose-modified cyclodextrin or the derivative thereof is selected from a group consisting of a lactose-modified dendrimer/glucuronyl glucosyl-β-cyclodextrin and a lactose-modified hydroxypropyl-β-cyclodextrin.

2. The method according to claim 1, wherein the lactose-modified cyclodextrin or the derivative thereof is a lactose-modified dendrimer/glucuronyl glucosyl-β-cyclodextrin.

3. The method according to claim 2, wherein the lactose-modified dendrimer/glucuronyl glucosyl-β-cyclodextrin is one in which at least the dendrimer molecule is modified with lactose.

4. The method according to claim 2, wherein a degree of substitution of cyclodextrin against dendrimer in the lactose-modified dendrimer/glucuronyl glucosyl-β-cyclodextrin is about 1 to 10.

5. The method according to claim 1, wherein the lactose-modified cyclodextrin or the derivative thereof is a lactose-modified hydroxypropyl-β-cyclodextrin.

6. The method according to claim 1, wherein a degree of substitution of lactose against cyclodextrin or dendrimer in the lactose-modified cyclodextrin or a derivative thereof is about 1 or more.

7. The method according to claim 1, wherein the neurological disease or disorder is selected from the group consisting of Alzheimer's disease, cerebral stroke, cerebral ischemia, dementia, muscular dystrophy, multiple sclerosis, amyotrophic lateral sclerosis, cystic fibrosis, Angelman's syndrome, Riddle Syndrome, myasthenia gravis, spinal muscle atrophy, Down's syndrome, Parkinson's disease, Huntington's disease, schizophrenia, depression, Tauopathy disease, Pick's disease, Paget's disease, lysosome disease accompanied by brain damage, cancer, prion's disease, traumatic brain injury, and viral or bacterial central nervous system disorders.

8. A carrier for a drug delivery into a brain comprising a lactose-modified cyclodextrin or a derivative thereof,
wherein the lactose-modified cyclodextrin or the derivative thereof is selected from a group consisting of a lactose-modified dendrimer/glucuronyl glucosyl-β-cyclodextrin and a lactose-modified hydroxypropyl-β-cyclodextrin.

9. The carrier for drug delivery according to claim 8, wherein the lactose-modified cyclodextrin or the derivative thereof is the lactose-modified dendrimer/glucuronyl glucosyl-β-cyclodextrin.

10. The carrier for drug delivery according to claim 8, wherein the lactose-modified cyclodextrin or the derivative thereof is the lactose-modified hydroxypropyl-β-cyclodextrin.

11. The carrier for drug delivery according to claim 9, wherein a degree of substitution of cyclodextrin against dendrimer in the lactose-modified dendrimer/glucuronyl glucosyl-β-cyclodextrin is about 1 to 10.

12. A pharmaceutical composition comprising:
a carrier for drug delivery into a brain, the carrier comprising a lactose-modified cyclodextrin or a derivative thereof; and
a drug,
wherein the lactose-modified cyclodextrin or the derivative thereof is selected from the group consisting of a lactose-modified dendrimer/glucuronyl glucosyl-β-cyclodextrin, and a lactose-modified hydroxypropyl-β-cyclodextrin.

13. The pharmaceutical composition according to claim 12, wherein the pharmaceutical composition is provided for treating or preventing a neurological disease or disorder.

14. The pharmaceutical composition according to claim 13, wherein the neurological disease or disorder is selected from the group consisting of Alzheimer's disease, cerebral stroke, cerebral ischemia, dementia, muscular dystrophy, multiple sclerosis, amyotrophic lateral sclerosis, cystic fibrosis, Angelman's syndrome, Riddle Syndrome, myasthenia gravis, spinal muscle atrophy, Down's syndrome, Parkinson's disease, Huntington's disease, schizophrenia, depression, Tauopathy disease, Pick's disease, Paget's disease, lysosome disease accompanied by brain damage, cancer, prion's disease, traumatic brain injury, and viral or bacterial central nervous system disorders.

15. A brain-penetrating ligand for delivering a drug into a brain of subject, comprising a lactose-modified cyclodextrin or a derivative thereof, wherein the lactose-modified cyclodextrin or the derivative thereof is selected from the group consisting of a lactose-modified dendrimer/glucuronyl glucosyl-β-cyclodextrin, and a lactose-modified hydroxypropyl-β-cyclodextrin.

16. The brain-penetrating ligand according to claim 15, wherein the lactose-modified cyclodextrin or the derivative thereof is a lactose-modified dendrimer/glucuronyl glucosyl-β-cyclodextrin.

17. The brain-penetrating ligand according to claim 15, wherein the lactose-modified cyclodextrin or the derivative thereof is a lactose-modified hydroxypropyl-β-cyclodextrin.

18. The brain-penetrating ligand according to claim 15, wherein a degree of substitution of lactose against cyclodextrin or dendrimer in the lactose-modified cyclodextrin or the derivative thereof is about 1 or more.

19. A pharmaceutical composition comprising:
a brain-penetrating ligand for delivering a drug into a brain of subject, the brain-penetrating ligand comprising a lactose-modified dendrimer/glucuronyl glucosyl-β-cyclodextrin or a lactose-modified hydroxypropyl-β-cyclodextrin; and
a drug.

20. The pharmaceutical composition according to claim 19, wherein the pharmaceutical composition is provided for treating or preventing a neurological disease or disorder.

21. The pharmaceutical composition according to claim 20, wherein the neurological disease or disorder is selected from the group consisting of Alzheimer's disease, cerebral stroke, cerebral ischemia, dementia, muscular dystrophy, multiple sclerosis, amyotrophic lateral sclerosis, cystic fibrosis, Angelman's syndrome, Riddle Syndrome, myasthenia gravis, spinal muscle atrophy, Down's syndrome, Parkinson's disease, Huntington's disease, schizophrenia, depression, Tauopathy disease, Pick's disease, Paget's disease, lysosome disease accompanied by brain damage, cancer, prion's disease, traumatic brain injury, and viral or bacterial central nervous system disorders.

* * * * *